US008177828B2

(12) United States Patent  (10) Patent No.: US 8,177,828 B2
Anderson et al.  (45) Date of Patent: May 15, 2012

(54) UNDERBODY CONVECTIVE WARMING BLANKET CONSTRUCTIONS

(75) Inventors: Thomas P. Anderson, Savage, MN (US); Andrew J. McGregor, Minneapolis, MN (US); Mark J. Scott, Maple Grove, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 483 days.

(21) Appl. No.: 12/460,981

(22) Filed: Jul. 27, 2009

(65) Prior Publication Data

US 2011/0022134 A1 Jan. 27, 2011

(51) Int. Cl.
*A61F 7/00* (2006.01)
*A47C 27/08* (2006.01)

(52) U.S. Cl. ............ 607/107; 607/104; 607/108; 5/706; 5/714

(58) Field of Classification Search ................ 607/104, 607/107, 108–112; 5/665–690, 706–715
See application file for complete search history.

(56) References Cited

U.S. PATENT DOCUMENTS

| | | | |
|---|---|---|---|
| 2,930,594 A | 3/1960 | MacCracken | 607/104 |
| 3,089,153 A | 5/1963 | Bosc | 5/348 |
| 3,674,019 A | 7/1972 | Grant | 601/148 |
| 3,778,851 A | 12/1973 | Howorth | 5/347 |
| 3,867,939 A | 2/1975 | Moore et al. | 604/291 |
| 4,005,236 A | 1/1977 | Graebe | 428/72 |
| 4,091,808 A | 5/1978 | Nelson | 128/133 |
| 4,114,620 A | 9/1978 | Moore et al. | 128/254 |
| 4,541,136 A | 9/1985 | Graebe | 5/456 |
| 4,867,230 A | 9/1989 | Voss | 165/46 |
| 5,022,110 A | 6/1991 | Stroh | 5/455 |
| 5,033,136 A | 7/1991 | Elkins | 5/421 |
| 5,165,400 A | 11/1992 | Berke | 128/400 |
| 5,184,612 A | 2/1993 | Augustine | 128/400 |
| 5,265,599 A | 11/1993 | Stephenson et al. | 607/104 |
| 5,300,102 A | 4/1994 | Augustine et al. | 607/107 |
| 5,304,213 A | 4/1994 | Berke et al. | 607/104 |
| 5,336,250 A | 8/1994 | Augustine | 607/107 |
| 5,561,875 A | 10/1996 | Graebe | 5/423 |
| 5,603,690 A | 2/1997 | Barry | 601/148 |

(Continued)

FOREIGN PATENT DOCUMENTS

DE   3320771 A1   12/1984

(Continued)

OTHER PUBLICATIONS

Abstract of DE3320771, Dec. 13, 1984, Noack.

(Continued)

*Primary Examiner* — Linda Dvorak
*Assistant Examiner* — Adam Avigan
(74) *Attorney, Agent, or Firm* — Adam Bramwell

(57) ABSTRACT

An underbody convective warming blanket includes a duct that is separate from, but in fluid communication with, interior space of the underbody convective warming blanket. The duct may be deployed to provide an air circulation conduit to shunt air around the air distribution structure in the interior space. The duct may be a flexible tube having a first end coupled to a first duct port in the underbody convective warming blanket near a first end of the underbody convective warming blanket and a second end to be coupled to a second duct port in the underbody convective warming blanket near a second end of the underbody convective warming blanket. An underbody convective warming blanket may include a midsection with an elongate columnar configuration which transitions at an end, or at each end, to a plinth-like configuration.

23 Claims, 5 Drawing Sheets

U.S. PATENT DOCUMENTS

| | | | |
|---|---|---|---|
| 5,620,482 A | 4/1997 | Augustine et al. | 607/107 |
| 5,640,727 A | 6/1997 | Kappel | 5/482 |
| 5,640,728 A | 6/1997 | Graebe | 5/606 |
| 5,655,237 A | 8/1997 | Suzuki et al. | 5/502 |
| 5,683,441 A | 11/1997 | Dickerhoff et al. | 607/107 |
| 5,702,375 A | 12/1997 | Angelillo et al. | 604/358 |
| 5,735,890 A | 4/1998 | Kappel et al. | 607/104 |
| 5,785,716 A | 7/1998 | Bayron | 607/108 |
| 5,800,489 A | 9/1998 | Augustine | 607/107 |
| 5,860,292 A | 1/1999 | Augustine et al. | 62/259.3 |
| 5,891,187 A | 4/1999 | Winthrop et al. | 607/96 |
| 5,941,907 A | 8/1999 | Augustine | 607/104 |
| 5,997,572 A | 12/1999 | Arnold et al. | 604/104 |
| 6,102,936 A | 8/2000 | Augustine et al. | 607/96 |
| 6,511,501 B1 | 1/2003 | Augustine et al. | 607/96 |
| 6,859,939 B1 | 3/2005 | Osburn, Sr. | 2/69 |
| 7,172,616 B2 | 2/2007 | Schuessler | 607/107 |
| 2005/0143797 A1 | 6/2005 | Parrish | 607/104 |
| 2006/0052851 A1 | 3/2006 | Anderson et al. | 607/104 |
| 2006/0161231 A1 | 7/2006 | Cazzini | 607/104 |
| 2009/0248120 A1 | 10/2009 | Starr et al. | 607/107 |

FOREIGN PATENT DOCUMENTS

| | | |
|---|---|---|
| EP | 0757907 A1 | 2/1997 |
| EP | 1096907 | 3/2006 |
| GB | 1350110 | 4/1974 |
| GB | 2228193 A | 8/1990 |
| WO | WO 00/04853 A1 | 2/2000 |

OTHER PUBLICATIONS

Written Opinion for PCT/US99/12622, published as WO 00/04853 A1, mailed May 12, 2000.

IPER for PCT/US99/12622, published as WO 00/04853 A1, mailed Oct. 25, 2000.

Examination Report for EP 99928410.2, EP Regional Phase of PCT/US99/12622, mailed May 12, 2004.

Abstract: A. Tominaga, et al., "Efficacy of an Underbody Forced-Air Warming Blanket for the Prevention of Intraoperative Hypothermia", Anestheseology 2007; 107:A91.

Article: S.R. Insler, et al., "An Evaluation of a Full-Access Underbody, Forced-Air Warming System During Near-Normothermic, On-pump Cardiac Surgery", Anesthesia & Analgesia; vol. 106, No. 3, Mar. 2008.

International Search Report and Written Opinion, PCT/US2010/001139, Jul. 21, 2010.

UNDERBODY CONVECTIVE WARMING BLANKET CONSTRUCTIONS

This application contains material related to that of commonly-owned U.S. patent application Ser. No. 10/935,992, filed Sep. 8, 2004 for "Inflatable Convective Pad For

BACKGROUND

The field includes an inflatable underbody convective warming blanket adapted to be deployed under a person for warming the person during clinical procedures such as surgery. More particularly, the underbody blanket may include a bypass duct in communication with interior space in the underbody device. More particularly still, an underbody convective warming blanket may have a structure including an elongate columnar midsection which transitions at an end, or at each end, to a plinth-like configuration.

Warming a person during surgery affords clinical benefits, such as prevention or treatment of hypothermia, encouragement of immune system function, promotion of wound healing, reduction of infection rates, and mitigation of discomfort. An inflatable blanket laid over a person's body is used to warm the person perioperatively. Such a blanket, when inflated with heated air, warms the person principally by convection of warmed air through a permeable portion of the blanket, although conduction and radiation of heat from the blanket also contribute to warming.

However, covering a person for warming may interfere with a variety of surgical procedures by preventing or limiting access to the person. For example, during cardiac surgery access to the thorax, groin and extremities is necessary when blood vessels must be harvested from the legs and arms for bypass construction on the heart. Covering a person with a convective warming blanket may interfere with, if not prevent, the necessary access. Adapting the blanket to avoid interference by reducing its size may compromise its capacity to warm the person. Adapting the blanket to provide access by separable seals may extend and complicate the surgery due to need to integrate the operation and management of the blanket with surgical protocols.

One way to achieve the benefits of warming a person during clinical procedures while providing unobstructed access to the person is to deploy an inflatable underbody convective warming blanket ("underbody blanket") beneath the person. The person is laid on the underbody blanket which warms the person by convection of warmed air, and also by conduction and radiation, without covering the person. Examples of underbody blankets include an inflatable convective pad described in the assignee's '992 application, the inflatable pad described in the assignee's U.S. Pat. No. 6,102,936, and the assignee's underbody series blankets illustrated and described at www.arizanthealthcare.com.

Underbody blanket and warming blanket constructions differ in significant ways. In this regard, merely rotating a warming blanket to dispose it beneath a person, with the permeable surface supporting the person, and then inflating the device with warmed air provided through an inlet port may not achieve desired warming, for a number of reasons.

A preferred warming blanket construction includes permeable and impermeable sheets that are sealed together at their peripheries to form an interior space between the sheets. Patterns of interior seals between the sheets within the peripheral seal form air distribution structures in the interior space that are intended to maintain a uniform temperature within the warming blanket with a minimal loss of heat. One or more inlet ports are provided in the construction to admit warmed air into the interior space. The warmed air pressurizes and inflates the blanket, and the inflation pressure forces warmed air through the permeable sheet which faces the person when the blanket covers the person. The inlet ports are typically provided in the impermeable sheet, within the peripheral seal.

Warming blankets are not constructed to be used as underbody devices. Rotation of the warming blanket such that the blanket is underneath the person places the impermeable sheet and the inlet port against a supporting surface such as a surgical table, which makes it difficult to couple an air hose to the port. Further, the pressure of the person's body against the inlet port can impede or, in some cases, pinch off the air distribution structures and thereby block distribution of warmed air in the warming blanket. Thus, the supporting device must be modified to accommodate an air hose, and/or the warming blanket must be placed so as to locate the inlet port beyond the periphery of the supporting device.

Moreover, the air distribution structure of a preferred warming blanket construction includes parallel sequences of elongated or closely spaced interior seals arranged to define generally parallel, longitudinal tubular structures when the blanket is inflated. Air enters the warming blanket though a central tube from which it flows laterally through small openings to the other tubes. If placed underneath a patient, the central tube can be pinched off by the person's weight during operation, which will prevent the distribution of warmed air in the warming blanket.

The underbody blanket construction illustrated in US 2006/0052851 accommodates and complements the positioning of a patient directly on the permeable surface. The inlet ports are located at or near sides or edges of the inflatable structure. This construction has no central tube from which pressurized air flows laterally. Instead, relatively short, widely spaced interior seals or stake points define an air distribution structure with a cross hatch of intersecting air passages with major longitudinal and transverse components. However, the underbody blanket is compliant, without significant structure when receiving a flow of warmed, pressurized air, so that the weight of the patient on the permeable surface compresses the underbody blanket. This occludes airflow and prevents heat from reaching the patient's potentially ischemic pressure points, so as to reduce the potential for nosicomial pressure sores and thermal injuries.

Nevertheless, the underbody blanket maintains convective warming of as much of the patient's body as possible, even when the size and weight of the patient occludes airflow through its central portion. In this regard, as seen in FIG. 4 of US 2006/0052851, the underbody blanket construction is generously dimensioned in length and width so as to circulate air along a portion of the air distribution structure positioned inside of the blanket's periphery, around the outside periphery of a patient's body, when the patient lies upon the blanket. This configuration maintains at least a minimal condition of inflation and operation so that the patient is convectively warmed by pressurized air from the air distribution portion at the blanket's periphery.

However, operation of the underbody blanket during certain clinical procedures may be impaired by pinch-off caused by the patient's position. For example, in FIG. 8 of US 2006/0052851, the patient is lying on his side with arms extended and the blanket's periphery sandwiched therebetween. This occludes airflow along the one side of the blanket and increases the airflow path length to parts of the blanket that would otherwise be served by a short path through the occluded section. The width of the middle section of the underbody blanket also makes the peripheral portion of the air distribution structure vulnerable to being pinched off by clinical personnel leaning against a side of the blanket, as when a surgeon braces against a surgical table to lean over a patient when accessing a surgical site. Pinch-off may interrupt some or all of the air flow through the underbody blanket, thereby reducing its therapeutic effect.

Thus, in some applications it is desirable to provide a separate air flow channel to bypass a pinch-off location in an underbody blanket in order to maintain short air flow paths within the interior space of the underbody blanket.

Furthermore, in other applications, it is desirable to narrow the midsection of the underbody blanket in order to reduce the risk of occlusion of the peripheral air flow structure of the underbody blanket.

SUMMARY

These and other problems are solved in underbody convective warming blankets by an air channel separate from the interior space in the underbody blanket for circulation of inflating air around at least a portion of the interior space.

Preferably, the air channel is a duct or shunt having a first end coupled to a first duct port of the underbody blanket, near an end of the underbody blanket, and a second end capable of being coupled to a second duct port, near a second end of the underbody blanket. When the duct's second end is coupled to the second duct port, warmed air may flow through the duct to bypass at least a portion of the interior space.

In some aspects, the first end of the duct may be permanently joined to the underbody blanket at the first duct port. In some other aspects, there may be two second duct ports near the second end of the underbody blanket, and the second end of the duct may be releasably coupled to either one of the two duct ports.

The structure of the duct may include a flexible tube terminated at each end in a flange. The flange terminating the first end may be fixed to the underbody blanket, surrounding the first duct port. A second duct port may include a collar with a mechanism to releasably retain the flange terminating the second end.

Further problems may be solved and advantages realized in underbody convective warming blankets by provision of a blanket structure with a relatively narrow midsection. Preferably, the structure has an elongate columnar midsection which transitions at one end, or at each end, to a plinth-like configuration.

SPECIFICATION

Figure 1A:
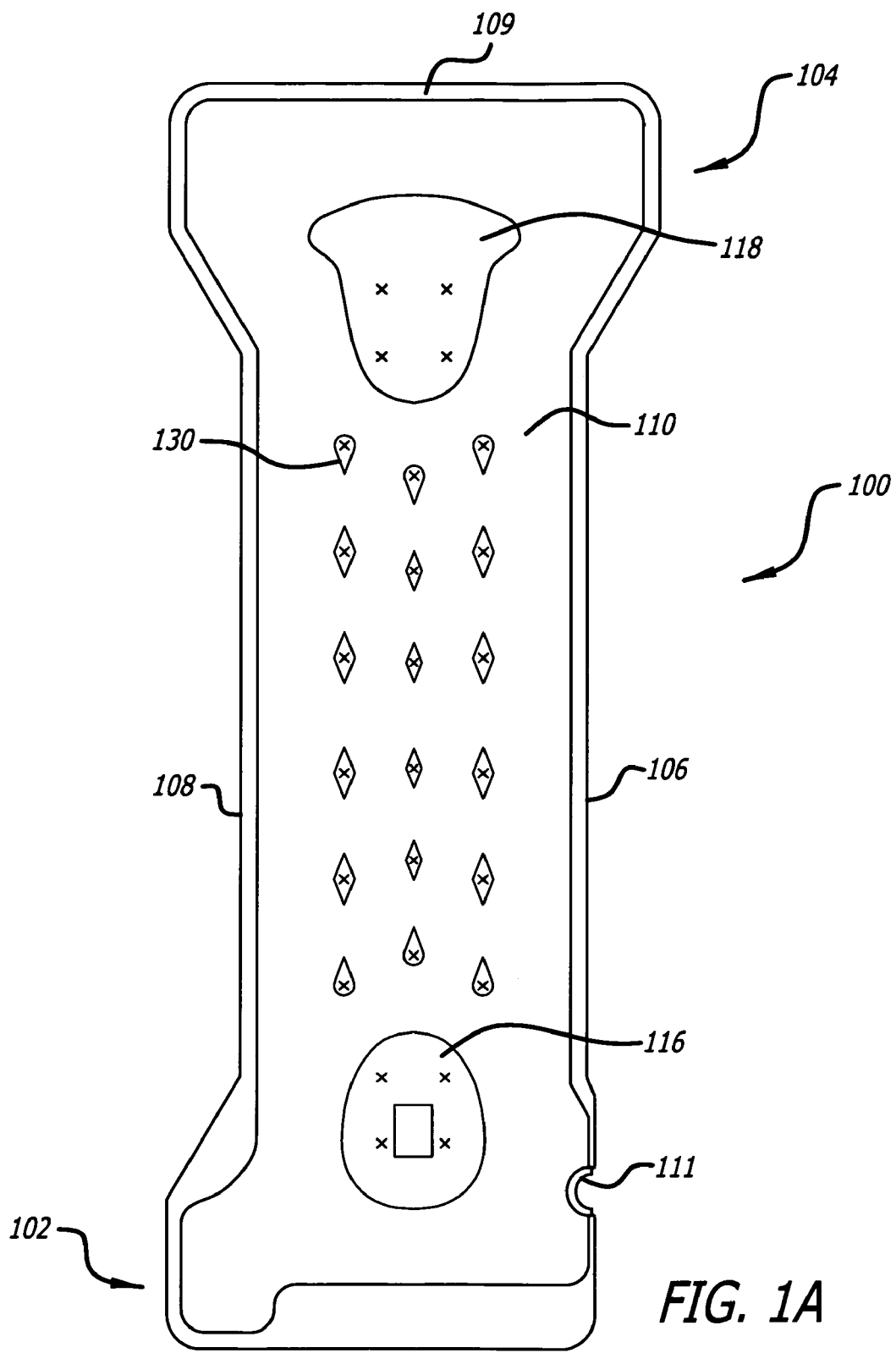
FIG. 1A is a plan view of the upper side of an underbody convective warming blanket.

An underbody convective warming blanket has two ends, upper and lower sides, and interior space with an air distribution structure. At least one inlet port opens through the underbody blanket, preferably through an edge thereof, into the interior space. Preferably, the underbody blanket is inflatable. That is to say, the underbody blanket, flaccid when not in use, tautens when a stream of pressurized air is received in the interior space by way of an inlet port. The underbody blanket has an upper surface on which a person may lie. At least a portion or portions of the upper surface is/are permeable to air. In a typical or preferred deployment, the underbody blanket is laid, or rests, on a supporting surface with the lower side on the supporting surface. When a stream of warmed pressurized air is received in the interior space, warmed air circulates in the air distribution structure, through the permeable upper surface, to warm a person lying on the upper side.

A preferred embodiment of an underbody convective warming blanket shown in the figures and described in this specification may be constructed using techniques and materials which are known in the art, or which are equivalent thereto. Generally, the construction and materials with which an underbody convective blanket may be made include two or more sheets of flexible material that are brought together in a manufacturing process. For example, the material may be a spunbond non-woven synthetic material, one side of which is extrusion coated (or lined) with a heat and/or glue sealable plastic. The material for the sheet forming the upper side may be processed by formation of apertures there through to configure the sheet's permeability. The sheets are brought together with the plastic linings facing each other and bonded, joined, or sealed by heat, glue, welding, or any equivalent, at a periphery by a peripheral seal, and at multiple points within the peripheral seal. Other materials and/or alternative construction methods may also be employed. One exemplary construction for the underbody convective warming blanket is described in the referenced US publication 2006/0052851 A1.

The peripheral seal joins the two or more sheets to form an interior space between the sheets. One sheet (the "upper sheet") forms the upper side of the underbody blanket; the other sheet (the "lower sheer") forms the lower side of the underbody blanket. The upper sheet has at least one permeable surface portion through which warmed, pressurized air circulates, passes, or exits to warm a person lying on the upper side. One or more inlet ports, each with provision for retention of an air hose nozzle, are provided through the underbody blanket for admitting a stream of warmed, pressurized air into the interior space, from an air hose connected to a heater/blower unit. Warmed air circulating through the one or more permeable surface portions causes the person to be warmed. Although convection of the warmed air is the principal mode of warming, the underbody convective warming blanket itself, when provided with warmed air, may also warm by radiation and conduction.

An underbody convective warming blanket 100 is seen in plan view in FIG. 1A, looking toward an upper side 110. The underbody blanket 100 has a head end 102, a foot end 104, and two elongate edges 106 and 108. The upper side 110 is permeable, with exceptions as may be required. The underbody blanket 100 may be constructed as described above from sheets sealed together by a peripheral seal 109 extending around the periphery of the underbody blanket. At least one inlet port is provided near an edge of the underbody blanket to admit a stream of warmed pressurized air into the interior space of the underbody blanket 100. For example, the at least one inlet port may be located at the edge 106 and may open through the peripheral seal 109. For example one inlet port 111 is disposed near the head end 102 of the underbody blanket 100. In some aspects, the inlet port may be constituted of a collar of relatively stiff material such as cardboard that surrounds an opening into the interior space of the underbody blanket 100. In this case, the collar receives and retains the nozzle of an air hose while the air hose delivers a stream of warmed, pressurized air into the interior space. If not used, the collar may be closed, for example by a removable plug. In some aspects, the underbody blanket may be provided with two or more inlet ports which may be constructed and selectively operated with plugs as taught in the assignee's U.S. Pat. No. 5,997,572. Alternatively, the inlet ports may be sleeves of material with means to retain the nozzle of an air hose.

As seen in FIG. 1A, the sheets of which the inflatable underbody convective blanket 100 is made are sealed together at locations or stake points 130 within the peripheral seal 109 to form or define an air distribution structure that distributes warmed pressurized air in the interior space of the underbody blanket. Some of these locations 130 may include drain passages to draw off fluids from the surface 110 that may accumulate before, during and/or after surgery. Drain passages may be constructed as taught in the referenced U.S. Pat. No. 6,102,936, or in other configurations, as required.

With further reference to FIG. 1A, in some aspects non-inflatable and/or impermeable areas 116 and 118 may be provided at the head and foot ends 102 and 104 of the underbody blanket 100. Warmed air cannot be convected from the areas 116 and 118, which are provided to receive and insulate the head and feet of a person lying on the upper side 110 of the underbody blanket 100.

Figure 1B:
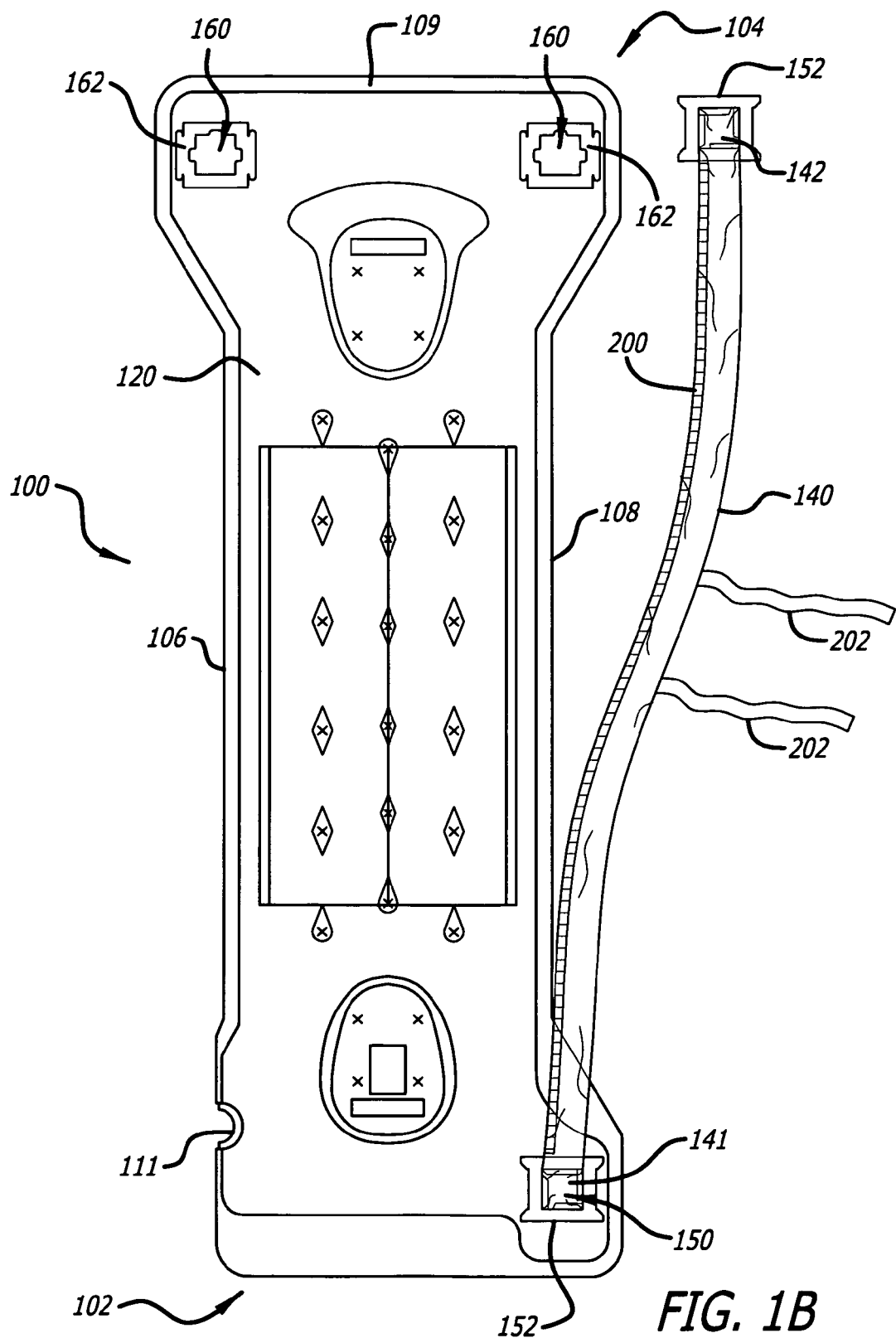
FIG. 1B is a plan view of the lower side of the underbody convective warming blanket showing a separate duct.
Figure 2:
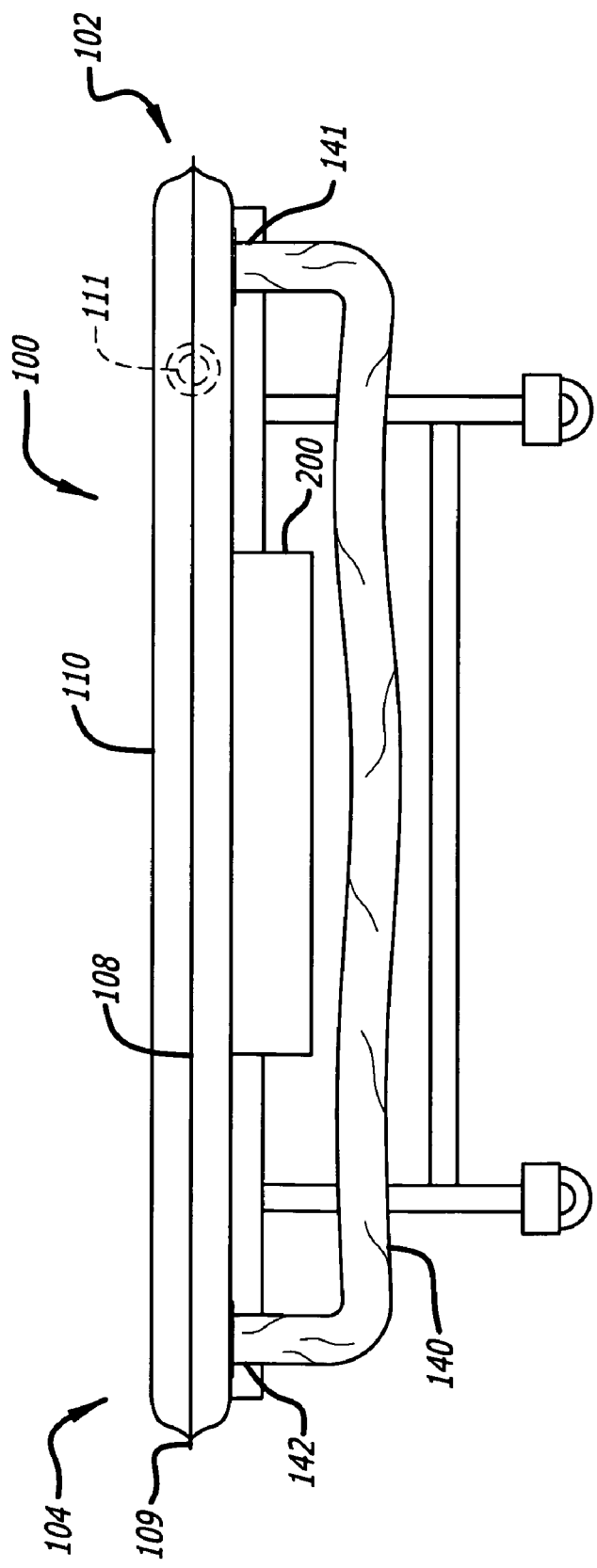
FIG. 2 is a side view of the underbody convective warming blanket showing the duct disposed to shunt warmed air around at least a portion of interior space in the underbody convective warming blanket.

FIG. 1B illustrates the underbody blanket 100 in plan view looking toward a lower side 120. The underbody blanket 100 includes a bypass duct 140 that is formed separately from the underbody blanket 100. Preferably, one end 141 of the bypass duct 140 is attached to the underbody blanket, in fluid communication with a first duct port 150 opening through the underbody blanket 100 to the interior space between the sheets of which the underbody blanket is constructed. The other end 142 of the bypass duct 140 may be coupled to and decoupled from a second duct port 160 opening through the underbody blanket 100 to the interior space between the sheets of which the underbody blanket is constructed. As best seen in FIG. 2, when the second end 142 is coupled to the second duct port and a stream of warmed, pressurized air flows through the inlet port 111 into the interior space of the blanket, some, if not all, of the inflating air flows through the bypass duct 140 out of and back into the interior space. In other words, the bypass duct shunts warmed, pressurized air around a portion of the interior space in the underbody blanket through an air path external to, and separate from, the interior space.

Refer now to FIG. 2, where the underbody blanket is inflated, and shown on a surgical table 200, looking toward the edge 108. A heater/blower unit and air hose which may be used to provide a flow of warmed, pressurized air through the inlet port 111 into the interior space of the underbody blanket are not shown in this figure.

FIGS. 1B and 2 illustrate preferred aspects of an underbody blanket with a separate bypass duct, with the understanding that any one or more of these aspects may be varied as required by design considerations. In a first preferred aspect, it is desirable that the duct 140 be attached at a single duct port near an end of the underbody blanket where an inlet port is positioned. In this aspect, the inlet port 111 opens through the edge 106 (and the peripheral seam 109) near the head end 102 and the end 141 of the duct 140 is attached to a first duct port 150 located near the head end 102. In this aspect, the first duct port 150 is positioned in a spaced lateral relationship with respect to the underbody blanket 100 and the inlet port 1,11, in which the inlet port 111 is adjacent one edge, for example, the edge 106, and the first duct port 150 is adjacent the opposite edge, the edge 108 in this example. Although the end 141 of the duct is attached, it may be releasably coupled; although a single first duct port 150 is shown, more than one may be provided.

In a second aspect, it is desirable that the first and second duct ports 150 and 160 be disposed in a spaced longitudinal relationship with respect to each other and the underbody blanket 100. In this regard, the first duct port 150 may be positioned near the head end 102 and the second duct port 160 may be positioned near the foot end 104. Although the spaced relationship is longitudinal, it may also be transverse.

In a third aspect, it is desirable that there be two second duct ports 160 near the foot end 104. In this third aspect, the second duct ports 160 may be disposed in a spaced opposing lateral relationship with respect to each other and the underbody blanket 100 in which each second duct port is positioned near a respective one of the edges 106 and 108. Although the spaced relation ship is lateral, it may also be transverse.

In a fourth aspect, it is desirable that the duct ports 150,160 be located in the lower side 120 of the underbody blanket 100; in this case, as seen in FIG. 2, when the duct 140 is deployed for use, it extends beneath the underbody blanket. Although the first and second duct ports are shown located on the underbody of the thermal blanket, they may also be located on the upper side, at the edges, or any combination thereof.

Figure 3:
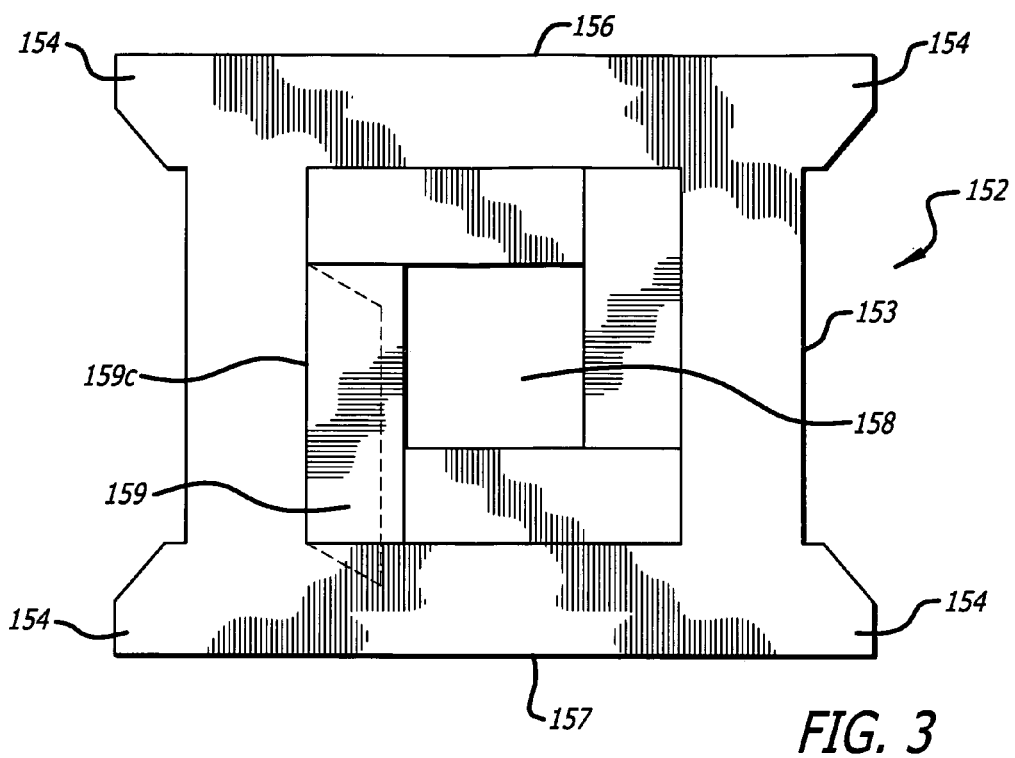
FIG. 3 is a plan view of an end flange for the duct.

As per FIG. 1B, the duct 140 may be constituted of a flexible tube, preferably an extruded polyurethane tube. The tube is preferably terminated at each end by a flange 152 shown in FIG. 3. The flange 152 is constructed from a flexible material having enough stiffness to retain the end of duct to which it is mounted either in permanent attachment to a surface of the underbody blanket 100. The preferred material for the flange 152 is a flexible wood products material such as cardboard; alternate materials may include plastics. The preferred flange 152 has a generally quadrilateral shaped frame structure 153, with oppositely-directed ears 154 at respective ends of opposing sides 156, 157 of the structure's outer perimeter. The interior of the frame structure 153 has a square central opening 158 defined by four rectangular flaps 159 arranged in a pinwheel-like pattern. A line of weakness 159c (perforations, for example) is formed along a seam where each flap joins the frame structure 153 so as to permit the flap to swing away from and toward the central opening 158 as shown by the dotted outline in FIG. 3.

Figure 5:
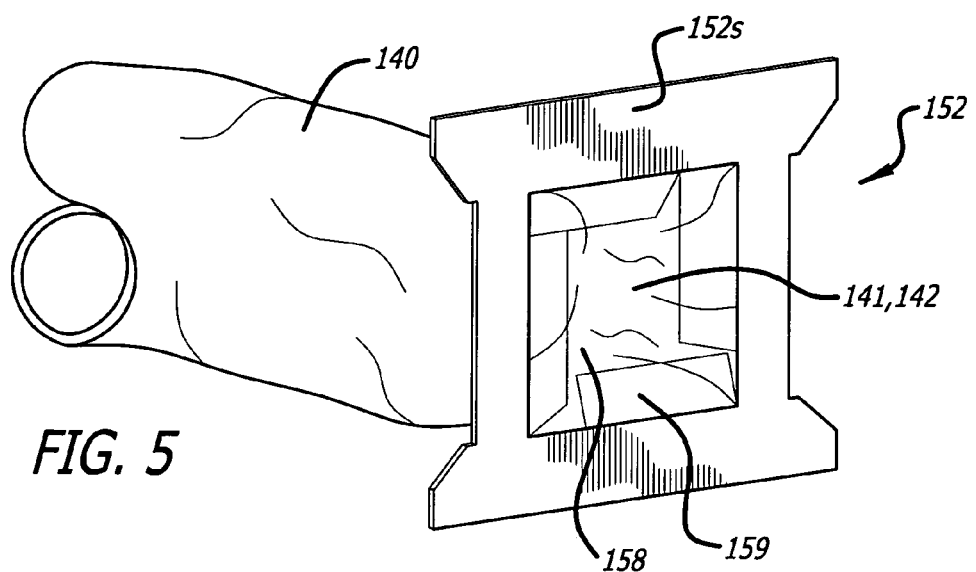
FIG. 5 is a perspective view of an end of the duct with an end flange mounted thereto.

With reference to FIG. 5, each of the ends 141, 142 of the duct may be terminated by attachment of a flange 152 thereto. In this regard, an end of the duct 140 is pulled through the opening 158 and attached around its outer surface to the flap surfaces that are visible in the figure. Such attachment may be by way of glue, adhesive, double-sided tape, staples, heat sealing, ultrasonic sealing, or any equivalent thereof. In this way, the flaps 159 act to retain the flange 152 on the end of the duct 140. Thus terminated, the first end 141 is attached or mounted to the lower side 120 at the location shown in FIG. 1B, with the flange opening 158 centered on the first duct opening. Such attachment may be by glue, adhesive, double-sided tape, heat sealing, ultrasonic sealing, or any equivalent thereof acting between the surface 152s of the flange and the surface of the lower side 120 that surrounds the first duct port 150.

Figure 4:
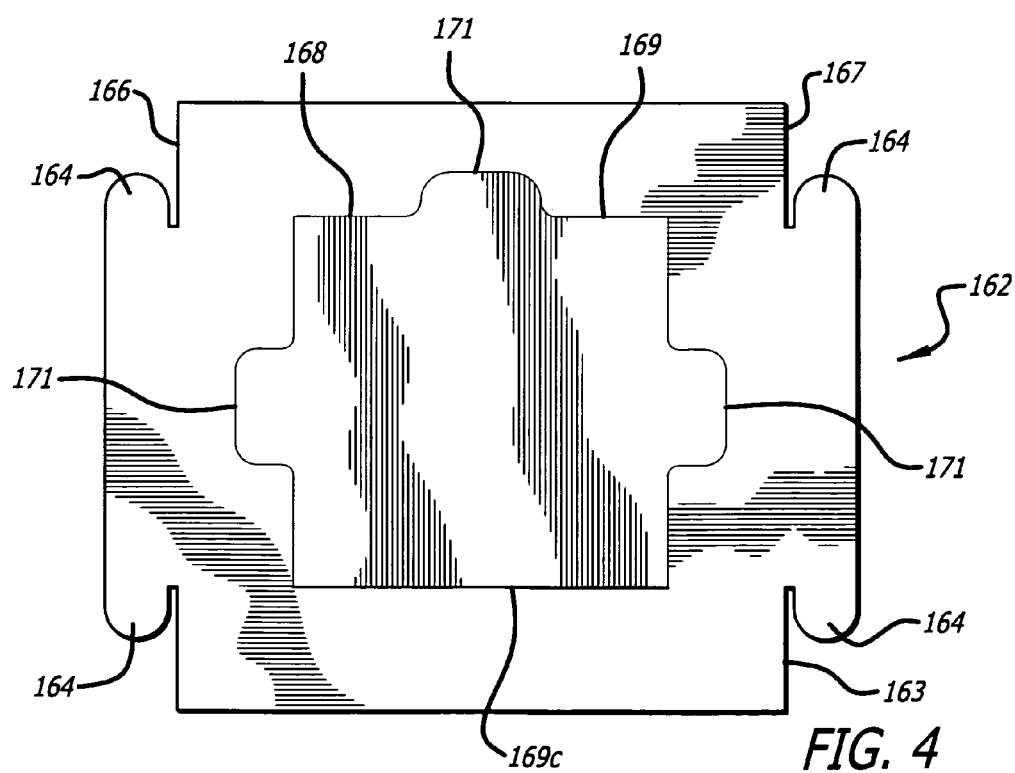
FIG. 4 is a plan view of a coupling collar for detachably retaining an end flange.

With reference to FIG. 4, a second duct port is framed by a coupling collar 162 The coupling collar 162 is constructed from a flexible material having enough stiffness to releasably retain a flange 152 mounted to an end of the duct 140. The preferred material for the coupling collar 162 is a flexible wood products material such as cardboard; alternate materials may include plastics. The preferred coupling collar 162 has a coupler with which the second end 142 of the bypass duct 140 may be releasably coupled to a second duct port. For example, the preferred coupling collar 162 may include a generally quadrilateral shaped frame structure 163, with oppositely-directed tabs 164 disposed inwardly of respective ends of opposing sides 166, 167 of the structure's outer perimeter. As per FIGS. 4 and 6, the interior of the frame structure 163 has a square central opening 168 defined by a hinged cover 169 with three outwardly-extending projections 171. A line of weakness 169c (perforations, for example) is formed along a seam where cover 169 joins the frame structure 163 so as to permit the cover to swing away from and toward the central opening 168 as shown in FIG. 6.

Although the coupler affording releasable coupling of the duct flange is embodied by a preferred flange extension/collar tab arrangement, other modes of releasable coupling are contemplated. Such other modes may include hook and eye mechanisms, snaps, buttons, straps, sliding members, adhesive mechanisms, or any mechanism permitting an end of the bypass duct to be disconnected from one duct port and repositioned and connected to another duct port.

Figure 6:
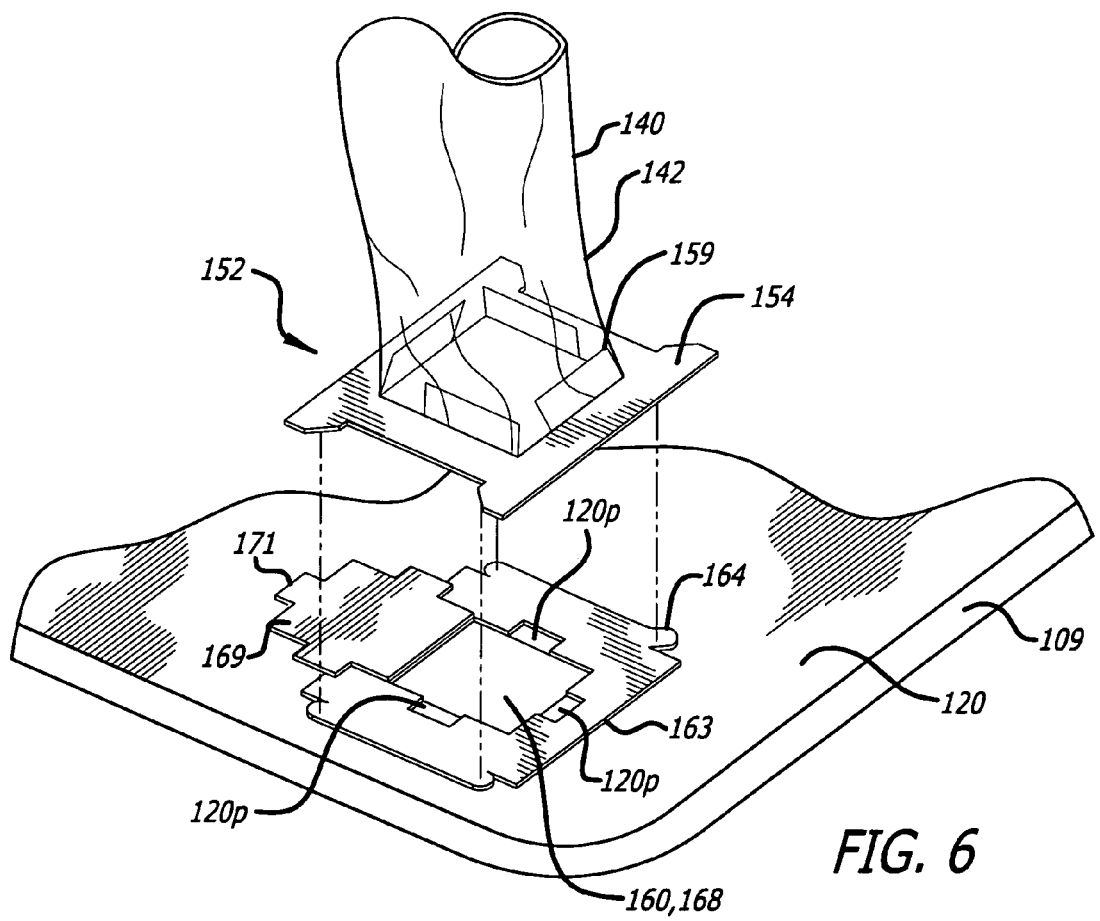
FIG. 6 is a perspective view of an end flange oriented with a coupling collar.

With reference to FIGS. 4 and 6, a coupling collar 162 is attached or mounted to the lower side 120 at such second duct port locations as may be required; for example, two such locations 160 are shown in FIG. 1B. The central opening 168 is centered on a second duct opening. Such attachment may be by glue, adhesive, double-sided tape, heat sealing, ultrasonic sealing, or any equivalent thereof, acting between one surface of the coupling collar 162 and the surface of the lower side 120 that surrounds the second duct port 160. Access to the second duct port is provided by opening the hinged cover 169. With the hinged cover 169 open, the second end 142 of duct 140 is releasably coupled to the second duct port by raising the tabs 164 to receive the ears 154, and placing the flange 152 against the coupling collar 162 with the ears 154 under the tabs 164 where they are held for so long as the operation of the bypass duct is needed. It should be noted that the coupling of the end 142 of the duct 140 at either second duct port can be released by disengaging the ears 154 from the tabs 164 and the end 142 may be coupled to another second duct port.

As per FIG. 6, in some aspects it may be desirable that the second duct port from which the end 142 is decoupled be closed after the end 142 is released from the tabs 164. For example a shift in the position of a patient lying on the upper surface may require shifting the end 142 of the duct 140 between second duct ports. In such aspects, a second duct port 160 may have a shape matching the shape of the opening 168, without the rectangular recesses from which the projections 171 are lifted. Edge portions 120p of the lower sheet are visible in these recesses. The second duct port 160 can be closed by rotating the hinged cover 169 back into the opening 168 and retaining the cover 169 therein by latching any one or more of the projections 171 under corresponding lower sheet edge portions 120p.

A duct for an underbody convective warming blanket may include one or more optional elements and/or variations as needed or desired. As per FIG. 1B, for example, the duct 140 may have an elongate visible marking to indicate alignment. In this regard, when the duct 140 is made of transparent or chromatically uniform flexible material, twists and/or kinks in the duct may be easy to overlook. However, an elongate visible marking, such as the series of marks 200, extending between the ends of the duct would indicate alignment (or misalignment) of the ends and would also indicate kinks to a user. One or more tie strips 202 of flexible material may be formed on or mounted to the outside surface of the duct 140 in order to secure it to an element such as a cross piece of a surgical table. The flexible tube of which the duct 140 is constituted may comprise coaxial flexible tubes, separately formed, or all of a piece. The inner tube may have apertures or holes opening into space between itself and the outer tube. Warmed, pressurized air flowing from one to the other end of the duct 140 flows into the space between the concentric tubes, thereby insulating the inner tube from ambient temperature and reducing heat loss from the duct to the ambient atmosphere. The tube may have an accordion or pleated configuration along its length so as to assume a self-supporting, non-kinking structure when conducting an air flow. The ends of the duct 140 may be permanently mounted to duct ports, and there may be more than one duct, each mounted as disclosed above, with or without the capability of being attachable. Attachable duct ends may be constructed differently than the embodiments disclosed and illustrated above; the means of attachment may vary. Thus, attachment may be by plug/socket structures, nozzle/port structures, opposing hook and eye material portions, snaps, adhesive, and any equivalent thereof.

A method of operating the underbody convective warming blanket 100 includes disposing the underbody blanket for use, for example placing the underbody blanket on a surgical table as in FIG. 2. One end 141 of the bypass duct 140 is mounted to the underbody blanket in fluid communication with the interior space in the underbody blanket 100, and the other end 142 is releasably coupled to the underbody blanket 100, in fluid communication with the interior space. The underbody blanket 100 is then inflated by provision of a stream of warmed, pressurized air provided through an inlet port 111 into the interior space from a conventional source (not seen) such as an air hose providing warmed, pressurized air into interior space. A person may be placed on the upper side 110. Warmed pressurized air is vented from the interior space through one or more permeable portions of the upper side 110; and warmed, pressurized air from the interior space is shunted around a portion of the interior space through the separate bypass duct 140, which is in fluid communication with the interior space.

As is also evident with respect to FIGS. 1A and 1B, the underbody blanket 100 may have a structure with a relatively narrow midsection, as measured between the sides 106 and 108. Preferably, the midsection has an elongate columnar shape or configuration which transitions at the foot end 104 to a plinth-like shape or configuration. As per FIG. 1B, the second duct ports 160 are located at respective sides of the plinth-like configuration at the foot end 104 so as to be positioned substantially outwardly of projections of the sides 106 and 108. As FIGS. 1A and 1B illustrate, the columnar configuration of the midsection also transitions to at least a partial plinth-like configuration at the head end 102. As per FIG. 1B, the first duct port 150 is located at the respective side of the partial plinth-like configuration at the head end 102 so as to be positioned substantially outwardly of a projection of the side 108.

An underbody convective warming blanket for warming a person has a bypass duct to shunt warmed pressurized air from interior space in the underbody blanket around a portion of the interior space has been described and illustrated. An underbody convective warming blanket for warming a person has a blanket structure with a relatively narrow midsection of an elongate columnar configuration which transitions at one end, or at each end, to a plinth-like configuration. The various embodiments of the underbody blanket that are shown and specified are meant to serve as examples of underlying principles, and many other equivalent embodiments will be evident to those of ordinary skill. The scope of patent protection for such a device is limited only by the claims below.

The novel tools and methods disclosed and illustrated herein may suitably be practiced in the absence of any element or step which is not specifically disclosed in the specification, illustrated in the drawings, and/or exemplified in the embodiments of this application. Moreover, although one or more inventions have been described with reference to one or more preferred embodiments, it should be understood that various modifications can be made without departing from the inventions of the description and figures. Accordingly, the inventive principles described and illustrated herein are limited only by the following claims.

The invention claimed is:

1. An underbody convective blanket comprising:
    an air permeable upper sheet;
    a lower sheet joined to the upper sheet to form an interior space between the upper and lower sheets;
    at least two duct ports opening to the interior space;
    a bypass duct separate from the upper and lower sheets and having first and second ends for coupling to the duct ports;
    wherein the bypass duct is configured to provide a separate air flow channel in order to bypass a pinched-off location in the interior space of the underbody convective blanket; and
    at least one inlet port opening to the interior space, separate from the at least two duct ports, for admitting warmed air into the interior space of the blanket.

2. The underbody convective blanket of claim 1, the at least two duct ports including first and second duct ports disposed in a spaced relationship in the lower sheet, wherein the first end is mounted to the first duct port and the second duct port includes a coupler to releasably couple with the second end.

3. The underbody convective blanket of claim 2, further including a first flange fixed to the first end and a second flange fixed to the second end.

4. The underbody convective blanket of claim 3, wherein the first flange is fixed to the lower sheet, around the first duct port.

5. The underbody convective blanket of claim 4, the coupler including a coupling collar fixed to the lower sheet, around the second duct port, and a mechanism for retaining the second flange on the coupling collar.

6. The underbody convective blanket of claim 4, wherein the second duct port includes two second duct ports disposed in a spaced lateral relationship, the coupler including a coupling collar fixed to the lower sheet around each second duct port and a mechanism for retaining the second flange on either of the coupling collars.

7. The underbody convective blanket of claim 1, wherein the bypass duct is a flexible tube.

8. The underbody convective blanket of claim 7, further including a first flange fixed to the first end and a second flange fixed to the second end.

9. The underbody convective blanket of claim 8, wherein the at least two duct ports include first and second duct ports and the first flange is fixed to the first duct port.

10. The underbody convective blanket of claim 9, wherein the second duct port includes two second duct ports disposed in a spaced relationship, further including coupling collars, each fixed around a second duct port, and a flange retaining mechanism on each coupling collar.

11. The underbody convective blanket of claim 1, further comprising an elongate columnar configuration in its midsection which transitions at one end, or at each end, to a plinth-like configuration.

12. An underbody convective blanket, comprising:
    a permeable upper side, a substantially impermeable lower side, and an interior space between the upper and lower sides;
    a flexible tube separate from the upper and lower sides;
    the flexible tube having a first end mounted to a first duct port opening into the interior space and a second end for coupling to a second duct port opening into the interior space;
    wherein the flexible tube is configured to provide a separate air flow channel in order to bypass a pinched-off location in the interior space of the underbody convective blanket; and
    at least one inlet port, separate from the first and second duct ports, to admit a flow of pressurized air into the interior space.

13. The underbody convective blanket of claim 12, further including a first flange fixed to the first end and a second flange fixed to the second end.

14. The underbody convective blanket of claim 13, wherein the first flange is fixed to the first duct port.

15. The underbody convective blanket of claim 14, further including a coupling collar fixed to the lower side, around the second port, and a mechanism for releasably retaining the second flange on the coupling collar.

16. The underbody convective blanket of claim 15, wherein the second port includes two second ports disposed in a spaced relationship, further including coupling collars, each fixed to the lower sheet, around a second port, and a mechanism for retaining the second flange on either of the coupling collars.

17. The underbody convective blanket of claim 12, further including a first flange fixed to the first end of the flexible tube and a second flange fixed to the second end of the tube.

18. The underbody convective blanket of claim 17, wherein the first flange is also fixed to the lower sheet, around the first port.

19. The underbody convective blanket of claim 18, further including coupling collars, each fixed to the lower sheet around a second port, and a flange retaining mechanism on each coupling collar.

20. The underbody convective blanket of claim 12, further including a visible alignment marking extending from the first end to the second end of the flexible tube.

21. The underbody convective blanket of claim 12, further including one or more tie straps on the flexible tube.

22. A method of operating an underbody convective blanket, comprising:
    (a) providing an underbody convective blanket comprising:
        (i) an air permeable upper sheet;
        (ii) a lower sheet joined to the upper sheet to form an interior space between the upper and lower sheets; at least two duct ports opening to the interior space;
        ii) a bypass duct separate from the upper and lower sheets and having first and second ends for coupling to the duct ports; wherein the bypass duct is configured to provide a separate air flow channel in order to bypass a pinched-off location in the interior space of the underbody convective blanket;
        (iv) at least one inlet port opening to the interior space, separate from the at least two duct ports, for admitting warmed air into the interior space of the blanket;

(b) providing warmed, pressurized air into the interior space of the underbody convective blanket;
(c) exhausting warmed pressurized air through the air permeable upper sheet of the underbody convective blanket; and
(d) shunting warmed, pressurized air in the interior space around a portion of the interior space through the bypass duct.

23. The method of claim 22, wherein the bypass duct is a flexible tube with a first end mounted to the underbody convective blanket in fluid communication with the interior space, the method further including coupling a second end of the flexible tube to the underbody convective blanket in fluid communication with the interior space.

* * * * *

UNITED STATES PATENT AND TRADEMARK OFFICE
CERTIFICATE OF CORRECTION

PATENT NO. : 8,177,828 B2  
APPLICATION NO. : 12/460981  
DATED : May 15, 2012  
INVENTOR(S) : Thomas P Anderson Page 1 of 1

It is certified that error appears in the above-identified patent and that said Letters Patent is hereby corrected as shown below:

<u>Page 2, Column 2,</u>  
Line 9, delete "Anestheseology" and insert -- Anesthesiology --, therefor.

<u>Column 1,</u>  
Line 6, after "For" insert -- Surgery", which was published as US 2006/0052851 A1 on 3/9/2006. --.

<u>Column 2,</u>  
Line 43, delete "nosicomial" and insert -- nosocomial --, therefor.

<u>Column 4,</u>  
Line 39, delete "sheer")" and insert -- sheet") --, therefor.

<u>Column 5,</u>  
Line 67, delete "1,11," and insert -- 111, --, therefor.

<u>Column 6,</u>  
Line 20, delete "relation ship" and insert -- relationship --, therefor.  
Line 21, delete "150,160" and insert -- 150, 160 --, therefor.

<u>Column 10,</u>  
Line 59, in claim 22, delete "ii)" and insert -- (iii) --, therefor.

Signed and Sealed this  
Ninth Day of October, 2012

David J. Kappos  
*Director of the United States Patent and Trademark Office*